US008987231B2

(12) United States Patent
Viscomi et al.

(10) Patent No.: US 8,987,231 B2
(45) Date of Patent: Mar. 24, 2015

(54) SULODEXIDE FOR USE IN THE TREATMENT OF PATHOLOGIES WHEREIN METALLOPROTEINASES ARE INVOLVED (75) Inventors: Giuseppe Claudio Viscomi, Bologna (IT); Ferdinando Mannello, Bologna (IT); Cristiana Bruno, Bologna (IT)

(73) Assignee: Alfa Wassermann S.p.A. (IT)

(*) Notice: Subject to any disclaimer, the term of this patent is extended or adjusted under 35 U.S.C. 154(b) by 0 days.

(21) Appl. No.: 13/642,510

(22) PCT Filed: Apr. 20, 2011

(86) PCT No.: PCT/IB2011/051726
§ 371 (c)(1),
(2), (4) Date: Nov. 6, 2012

(87) PCT Pub. No.: WO2011/132161
PCT Pub. Date: Oct. 27, 2011

(65) Prior Publication Data
US 2013/0045946 A1 Feb. 21, 2013

(30) Foreign Application Priority Data

Apr. 23, 2010 (IT) .............................. BO2010A0250

(51) Int. Cl.
A61K 31/727 (2006.01)
A61K 31/737 (2006.01)

(52) U.S. Cl.
CPC ................................... A61K 31/737 (2013.01)
USPC ............................................... 514/56; 514/54

(58) Field of Classification Search
None
See application file for complete search history.

(56) References Cited

U.S. PATENT DOCUMENTS

| 3,936,351 | A | 2/1976 | Bianchini |
| 4,705,798 | A | 11/1987 | Schoenwald et al. |
| 5,455,258 | A | 10/1995 | MacPherson et al. |
| 5,686,432 | A | 11/1997 | Baggio et al. |
| 2002/0128226 | A1 | 9/2002 | Kern et al. |
| 2004/0009952 | A1 | 1/2004 | Gambaro et al. |

FOREIGN PATENT DOCUMENTS

| EP | 998936 | 5/2000 |
| EP | 1016410 | 7/2000 |
| EP | 1292315 | 6/2001 |
| RU | 2153506 | 7/2000 |
| WO | 90/05719 | 5/1990 |
| WO | 94/02447 | 2/1994 |
| WO | 97/20824 | 6/1997 |
| WO | 2005/061549 | 7/2005 |

OTHER PUBLICATIONS

Blajchman et al. Annals of the New York Academy of Sciences (2006), vol. 556, pp. 245-254.*
Altinbas et al. Journal of Thrombosis and Haemostasis (2003), vol. 2, pp. 1266-1271.*
Saviano et al. Current Medical Research and Opinion (1993), vol. 13, pp. 96-108.*
Partial PCT International Search Report mailed on Nov. 9, 2011 for PCT/IB2011/051726 filed on Apr. 20, 2011 in the name of Alfa Wasserman S.P.A.
PCT International Search Report mailed on Jan. 16, 2012 for PCT/IB2011/051726 filed on Apr. 20, 2011 in the name of Alfa Wasserman S.P.A.
PCT Written Opinion mailed on Jan. 16, 2012 for PCT/IB2011/051726 filed on Apr. 20, 2011 in the name of Alfa Wasserman S.P.A.
Coccheri S. et al. "Randomised, double blind, multicentre, placebo controlled study of sulodexide in the treatment of venous leg ulcers". May 1, 2002. Thrombosis and Haemostasis. 87(6):947-952.
Coccheri S. et al. "Sulodexide in the treatment of intermittent claudication. Results of a randomized, doube-blind, multicentre, placebo-controlled study". Jul. 2002. European Heart Journal. 23(13):1057-1065.
Condorelli M. et al. "IPO-V2: A prospective, multicenter, randomized, comparative clinical investigation of the effects of sulodexide in preventing cardiovascular accidents in the first year after acute myocardinal infarction". Jan. 1, 1994. J Am College of Cardiology. 23(1):27-34.
Gaddi et al. "Meta-analysis of some results of clinical trials on sulodexide therapy in peripheral occlusive arterial disease". Sep. 1, 1996. J. Int'l Medical Res. 24(5):389-406.
Ofosu F.A. "Pharmacological actions of sulodexide". Jan. 1, 1998. Seminars in Thrombosis and Hemostasis. 24(2):127-138.
Verstraete M. et al. "Novel Antithrombotic Drugs in Development". Jun. 1, 1995. Drugs. 49(6):856-884.
Bergan, J., et al., Molecular Mechanisms in Chronic Venous Insufficiency, Annals of Vascular Surgery 2007, 21: 261-266.
Mene, P., et al., Monocyte/mesangial cell interactions in high-glucose co-cultures, Nephrology Dialysis Transplantation 2001, 16: 913-922.
Ceriello, A., et al., Glucosaminoglycans administration decreases high fibrinogen plasma levels in diabetic patients, Diab. Nutr. Metab. 1993, 6: 203-206.
Derosa, G., et al., Evaluation of metalloproteinase 2 and 9 levels and their inhibitors in diabetic and healthy subjects, Diabetes & Metabolism 2007, 33: 129-134.
Galis, Z., et al., Matrix Metalloproteinases in Vascular Remodeling and Atherogenesis The Good, the Bad, and the Ugly, Circulation Research 2012, 251-262.
Harenberg, J., Review of Pharmacodynamics, Pharmacokinetics, and Therapeutic Properties of Sulodexide, J. Med. Res. Rev. 1998, 18: 1-20.
Hidalgo, M., et al., Development of Matrix Metalloproteinase Inhibitors in Cancer Therapy, J. Nat'l Cancer Inst. 2001, 93: 178-203.

(Continued)

Primary Examiner — Patrick Lewis
(74) Attorney, Agent, or Firm — Steinfl & Bruno LLP (57) ABSTRACT The present invention describes sulodexide or at least one of its components for use in the reduction of circulating matrix metalloproteinase (MMPs), in particular MMP-9. Sulodexide and its composition are useful for the treatment of pathologies wherein the MMPs are involved, such as cardiovascular disease, cardiovascular disease caused by diabetes, varicose veins, chronic venous insufficiency (CVI), gastrointestinal ulcers, pulmonary disease, and neoplastic pathologies.

17 Claims, 3 Drawing Sheets (56) References Cited

OTHER PUBLICATIONS

Isnard, N., et al., Effect of sulfated GAGs on the expression and activation of MMP-2 and MMP-9 in corneal and dermal explant cultures, Cell Biol. Int'l 2003, 27: 779-784.

Kadoglou, N. et al., Matrix Mettalloproteinases and Diabetic Vascular Complications, Angiology 2005, 56: 173-189.

Laemmli, UK, Cleavage of Structural Proteins during the Assembly of the Head of Bacteriopahge T4, Nature 1970, 227: 680-685.

Mannelo, F., et al., Matrix Metalloproteinase Inhibitors as Anticancer Therapeutics, Current Cancer Drug Targets 2005, 5: 285-298.

Mannello, F., Serum or Plasma Samples? The "Cinderella" Role of Blood Collection Procedures Preanalytical Methodological Issues Influence the Release and Activity of Circulating Matrix Metalloproteinases and Their Tissue Inhibitors, Hampering Diagnostic Trueness and Leading to Misinterpretation, Arteriocler. Thromb. Biol. 2008, 28: 611-614.

Erhardt, J., et al., Effects of Blood Collection Methods on Gelatin Zymography of Matrix Metalloproteinases, Clin. Chem. 2003, 49: 339-340.

Mannello, F., et al., Heparin affects matrix metalloproteinases and tissue inhibitors of metalloproteinases circulating in peripheral blood, Clinical Biochemistry 2008, 41: 1466-1473.

Nelson, A., et al., Matrix Metalloproteinases: Biologic Activity and Clinical Implications, J. Clinical Oncology 2000, 18: 1135-1149.

Raffetto, JD, Dermal pathology, cellular biology, and inflammation in chronic venous disease, Thrombosis Research 2009, 123: 566-571.

Raffetto, JD et al., Matrix metalloproteinases and their inhibitors in vascular remodeling and vascular disease, Biochem. Pharma. 2008, 75: 346-359.

Rahko, E., et al., Immunohistochemical Study of Matrix Metalloproteinase 9 and Tissue Inhibitor of Matrix Mettaloproteinase 1 in Benign and Malignant Breast Tissue—Strong Expression in intraductal Carcinomas of the Breast, Tumor Biology 2009, 30: 257-264.

Ramnath, N., et al., Matrix Metalloproteinase Inhibitors, Curr. Oncology Reports 2004, 6: 96-102.

Tayebjee, M., et al., Matrix Metalloproteinase-9 and Tissue Inhibitor of Metalloproteinase-1 and -2 in Type 2 Diabetes, Diabetes Care 2004, 27: 2049-2051.

Tu, G., et al., Progress in the Development of Matrix Metalloproteinase Inhibitors, Curr. Medicinal Chem. 2008, 15: 1388-1395.

Vihinen, P., et al., Matrix metalloproteinases in cancer: prognostic markers and therapeutic targets, Int. J. Cancer 2002, 99: 157-166.

Dalteparin http://www.ncbi.nlm.nih.gov/mesh [retrieved on Aug. 3, 2014], p. 1.

Parnaparin Sodium http://www.drugs.com/international/parnaparin-sodium.html [retrieved on Aug. 3, 2014], pp. 1-2.

Milani, M.R. et al., "Pharmacokinetics of sulodexide evaluated from $^{131}$I-labelled fast moving heparin after single intravenous and oral administration of different doses in Man" *British Journal of Clinical Research* 1992; 3: 161-178.

Tramarin, R. et al., "Effetto di una Eparina a Basso Peso Molecolare (Sulodexide) Nella Trombosi Ventricolare Sinistra Post-Infartuale: Studio Exocardiografico" *Med. Praxis* 8 (2), 1987, 1-11.

Hovingh, P. et al., "Biological Implications of the Structural, antithrombin affinity and anticoagulant activity relationships among vertebrate heparins and heparin sulphates" *Biochem. J.* (1986), 237, 573-581.

Li, Z. et al., "Regulation of Collagenase Activities of Human Cathepsins by Glycosaminoglycans" *Journal of Biological Chemistry*, 279, 5470-5479 (2004).

Ra, H-J. et al., "Control of Promatrilysin (MMP7) Activation and Substrate-Specific Activity by Sulfated Glycosaminoglycans" *The Journal of Biological Chemistry* vol. 284, No. 41, pp. 27924-27932 (2009).

Radhakrishnamurthy, B. et al., "Studies of Chemical and Biologic Properties of a Fraction of Sulodexide, a Heparin-like Glycosaminoglycan" *Atherosclerosis*, 60 (1986) 141-149.

Kristova, V. et al., "Sulodexide Improves Endothelial Dysfunction in Streptozotocin-Induced Diabetes in Rats" *Physiol. Res.* 57: 491-494 (2008).

Russian Office Action issued on Jul. 7, 2014 for Russian Application No. 2012142256 filed on Apr. 20, 2011 in the name of Alfa Wassermann S.P.A., IT.

\* cited by examiner

Figure 1: Gel permeation profile of Sulodexide

Figure 2: Gel permeation profile of dermatan sulfate obtained by sulodexide

Figure 3: Gel permeation profile of Heparin obtained by sulodexide

SULODEXIDE FOR USE IN THE TREATMENT OF PATHOLOGIES WHEREIN METALLOPROTEINASES ARE INVOLVED

CROSS REFERENCE TO RELATED APPLICATIONS

The present application is the US national stage entry of International Application PCT/IB2011/051726 filed on Apr. 20, 2011, which in turn claims priority to Italian Application BO2010A000250, filed on Apr. 23, 2010.

The present invention describes sulodexide, or at least one of its components for use in the reduction of circulating matrix metalloproteinase (MMPs), in particular MMP-9.

Sulodexide and its composition are useful for the treatment of pathologies wherein the MMPs are involved, such as cardiovascular disease, cardiovascular disease caused by diabetes, varicose veins, chronic venous insufficiency (CVI), gastrointestinal ulcers, pulmonary disease, and neoplastic pathologies.

BACKGROUND OF THE INVENTION

Recent studies have demonstrated the involvement of a group of zinc-dependent endopeptidases, called matrix metalloproteinase (MMPs), belonging to the matrixin family in the vascular alteration of cardiovascular pathologic conditions.

Venous hypertension is at the basis of several pathologies related to disorders of macro and micro circulation disorders and causing infiltrations of leucocytes in the endothelium, deterioration of the cardiac valves and finally providing the remodeling/rearrangement of vein wall, which can provide a reflux, or formation of varicose veins and derma pathologies as described by Bergam J. et al. in Ann. Vasc. Surg. 21 (2007), 260-266. Raffetto J D. et al. in Thromb. Res. 123 (2009) S66-S71 describe that the modifications observed during the progression of chronic venous pathology may be associated to an alteration of the hematic balance between the level of matrix metalloproteinase (MMPs) and their tissue inhibitors (TIMPs).

Both MMPs and TIMPs, being involved in the physiologic remodeling of extracellular matrix, play important role also in the cellular communication.

High MMPs concentrations have been found in different pathologies as reported by Mannello F. et al. in Curr. Cancer Drug Targets 5 (2005), 285-298. Among MMPs, MMP-9 (Gelatinase B, EC3.4.24.35 of 92, 130 and 225 KDa) are involved in several pathologies, comprising neoplastic pathologies suggesting that their presence as circulating enzyme and their increase are related to the progression of different cancer types, such as in breast, lungs, ovary and prostate cancer and melanoma, as described by Rahko E. et al. in Tumor Biol., 30 (5-6) (2009), 574-64.

In vascular pathological conditions, also caused by diabetes, it is clearly showed the pathogenic role of MMPs. Galis Z. S. et al. in Circ. Res. 90 (2002), 251-262, Kadoglou N. P. et al. in Angiology 56 (2005), 173-189, Derosa G. et al. in Diabetes Metab. 33 (2007), 129-134 and Tayebjee M. H. et al. in Diabetes Care 27 (2004), 2049-2051 describe an increased level of circulating MMP in diabetic patients.

Raffetto J D. et al. in Biochem. Pharmacol. 75 (2008), 346-359, demonstrate the importance of MMPs in vascular disease, reporting that the increased extracellular matrix degradation (ECM) in venous wall, is involved in the early steps of venous relaxation, formation of varicose veins, dermal modification and finally leading to the formation of venous ulcers.

Among the several pathological mechanisms linked to the increased expression of MMPs, the interactions leucocytes-endothelium are important and represent a possible objective for the pharmacological treatment. Mannello F. et al. describe in Arteriosler. Thromb. Vasc. Biol. 28 (2008), 611-614, that leucocytes and platelets contain higher amounts of MMPs, which can be released into the extracellular milieu consequently to the leukocyte activation/degranulation or during platelet aggregation. Furthermore, MMP-9 is released from platelets and leucocytes after a stimulus such as the reactions induced by the coagulation process.

It is known that the plasmin, activated during in the coagulation phase, is in turn a MMPs activator.

Among proteolytic enzymes present in human walls and potentially associated to the cancer invasions, the MMPs have been demonstrated to be involved in the capacity to degrade almost proteins of the interstitial matrix and basal membranes, allowing to the cells to diffuse and infiltrate in the neighboring walls.

Several compounds, such as growth factor receptors of adhesion cellular molecules, chemokines, cytokines, apoptotic ligands and angiogenic factors may interact with MMPs, modifying both its expression and activity.

These proteolytic enzymes act on many bioactive substrates being involved in the neoplastic development steps such as growth of primary tumor, angiogenesis, extravasation or intravasation of the neoplastic cells, migration, invasion of metastatic cells in the secondary organ, beginning and maintenance of the tumor growth.

Several clinical studies have been performed in both animal and human tumoral models to evaluate the importance of the reduction of circulating matrix metalloproteinase. The obtained results have lead to develop synthetic inhibitors as described by Ramnath N. et al. in Curr. Oncol. Rep. 6 (2004), 96-102.

The main inhibitors studied comprise mimetic peptides and non mimetic peptides of collagen, of tetracyclines and bisphosphonates derivatives.

Clinical trials executed with the available compounds have shown that prolonged treatments cause muscular-skeletal pain and inflammation. Although these events showed to be reversible and the patients started again the treatment after a short suspension period, the unexpected adverse events have limited the administration dosages.

Moreover, when the clinical trials for the treatment of neoplastic diseases were extended to a greater number of patients, besides serial toxicological problems due to the cytostatic effects, no significant therapeutic benefit was observed, as described by Mannello F. et al. in Curr. Cancer Drug Targets 5 (2005), 285-298.

Some MMPs inhibitors studied in clinical trials are Batimastat, Marimastat, Prinomastat, BAY 12-9566, CGS27023A and derivatives of tetracyclines.

Batimastat, BB-94 (WO 90057191), is a hydroxamic acid derivative, which mimes the peptidic structure of natural substrates. Batimastat is a powerful inhibitor of MMPs and has been the first inhibitor of MMP used in clinical trials, but it has shown low selectivity caused by low solubility and absorption. Furthermore, Batimastat had a lower compliance, being administrable only by injection in the pleural or abdominal space. The Phase III clinical trials were almost immediately suspended for serious side effects, such as strong local inflammatory tissue reaction, nausea, abdominal pains as reported Tu G. et al. in Curr. Med. Chem. 15 (2008), 1388-1395.

Marimastat, BB-2516 (WO 9402447), is a hydroxamic acid derivative with a structure similar to Batimastat, but with a higher solubility and then easier absorption by oral administration. Marimastat as well as Batimastat has low specificity and it was toxic in a percentage of about 30% of all treated patients, showing muscular-scheletal pains and rigidity, which starts in the little hands knuckle and moves up to arms and shoulders, especially around the tendinous insertion points, fibrosis and necrosis of the periarticular walls of ankle and knee and gastric disorder associated to weight loss as described by Vihinen et al. in Int. J. Cancer 99 (2002), 157-166.

Prinomastat, AG3340 (WO 90720824) is a hydroxamic acid derivative, selective against some MMPs involved in the tumoral invasion and metastasis. During the clinical trials, side effects occurred in the joint of shoulder, knee and hands, appeared and the treatment was immediately suspended, as described in Ramnath N. et al. in Curr. Oncol. Rep. 6 (2004), 96-102.

BAY 12-9566, (U.S. Pat. No. 4,705,798) is a butanoic acid derivative and in several clinical trials it has showed toxicity, represented by thrombocytopenia, anemia, increase of hepatic enzymes and bilirubin, nausea, tiredness and headache as described by Nelson A. et al. J. Clin. Oncol. 18 (2000), 1135-1149.

CGS27023A, (U.S. Pat. No. 5,455,258) has reported toxic effects with a wide cutaneous irritation, myalgia and arthralgia.

Also tetracyclines derivatives have shown severe adverse events during the clinical trial, such as tiredness, mental confusion, nausea, vomit, cutaneous phototoxicity, pancreatic enzymes increase, which limited the administrable dosage, as described by Hidalgo M. et al. in J. Natl. Cancer Inst. 93 (2001), 178-193.

Zymography and reverse zymography are techniques currently used for the MMPs and TIMPs analysis in biological samples. All types of substrates zymography originate from the gelatin zymography method. The techniques are the same except that the substrate differs depending on the type of MMPs or TIMPs. In these techniques, proteins are separated by electrophoresis under denaturing, not reducing conditions, in the presence of sodium dodecyl sulphate (SDS). Gelatin-zymography is a technique used mainly for gelatinase MMPs determination and it is extremely sensible to detect MMP-2 and MMP-9 at concentration of few picograms. It should be considered that other MMPs, such as MMP-1, MMP-8 and MMP-13 can also degrade the substrate.

The technique is based on electrophoresis separation, in polyacrylamide gel with a specific substrate; SDS denatures the MMPs which become inactive and after the electrophoresis migration, the SDS is removed from the gel in a suitable buffer, which restores the MMPs structures and functions. After that, if the gel is incubated, the activated gelatinases digest gelatine which is converted into low molecular weight peptides, that are removed by washing as described by Mannello F. et al. in Clin. Chem. 49 (2003), 339-34.

The gels are placed in a development solution, for example comprising Coomassie, and then destained with solutions comprising methyl or ethyl alcohol and acetic acid. The stained zone of the gel are due to the presence of not-degraded gelatine, while the not stained zone are due to the enzymatic activity of MMP. The enzymatic activity results proportional to the extension of the clear bands, thus it can be analyzed and quantified with densitometer instruments equipped with imagine analyzer.

Zymograms provide specific and distinct information on MMPs and in particular on MMP-2 and MMP-9, because the two enzymes can be separated on the basis of the different electrophoresis mobilities, which depend on their molecular weights. For this purpose, suitable molecular weight standards of corresponding to pro-MMP-2 72 kDa, and complex of pro-MMP-9 and MMP-9 at 92, 130 and 225 kDa are placed for comparison in the same gel.

Mannello F. et al. in Clin. Biochem. 41 (2008), 1466-73 studied the effect of the addition of high-molecular-weight lithium heparin to peripheral blood samples, for evaluating the effect of HMWH on MMPs and TIMPs expression in blood. The described effect was that HMWH had both direct and indirect effects altering the quantity of circulating MMP and TIMP and increasing the release of TIMP-2. The objective of this publication was essentially to describe the effect of a high-molecular-weight heparin (HMWH) in the MMPs expression in blood manipulation in order to standardize the procedure of blood sample handling, in a method of measuring MMPs. In this publication there are no references and/or suggestion regarding pharmacological uses of heparin. Moreover, it is not reported the lithium heparin concentrations, at which the effect is observed. As a consequence, it is not possible to know if the concentration of lithium heparin, which provided the effect observed, might be therapeutically useful, being well known the high risk of bleeding associated to HMWH. Nevertheless, being known that heparins are commonly administered by injection any possible heparin use done to the purpose of altering MMPs plasma concentrations, has to be supposed following the same route.

The effect of heparin on the MMP-2 and TIMP-2 mRNA expression is also reported by Caenazzo I. et al. in Nephrol. Dial. Transplant 2001, 16, 1769-75.

Therefore there is still the need to find active ingredients for medicine preparations, useful in the reduction of blood circulating MMPs concentration in the intent of treating all the pathologies wherein MMPs are involved, as pathogenesis of inflammation, infective or neoplastic or cardiovascular disease. Among these pathologies, are comprised for example, pathologies derived by diabetes, varicose veins, chronic venous insufficiency (CVI), atherosclerosis cardiac break after myocardium infarct, abdominal aortic aneurysm, pulmonary pathology, increase and progression of the tumor, growing in the primary tumor, abnormal angiogenesis, extravasation and intravasation of the neoplastic cells.

Vascular diseases are selected in the group of varicose veins, human atherosclerosis, cardiac break after myocardium infarct, abdominal aortic aneurysm.

Moreover there is the need to obtain medicines, without any side or toxic effect at therapeutically effective dosage, acceptable by the patients and administrable by oral route, intramuscular or intravenous injection for the treatment of all pathologies wherein MMPs are involved.

It has been unexpectedly found, and it is an object of the present invention, that sulodexide, or one of its component, in particular dermatan sulfate obtained by sulodexide (SDX-DS) or heparin (SDX-HEP) obtained by sulodexide, inhibit and/or reduce the level of circulating MMPs.

Sulodexide is a natural mixture of natural glycosaminoglycans, GAGs, extracted from intestinal mammalian mucosa, as described in U.S. Pat. No. 3,936,351, comprising a mixture of fast-moving heparin (SDX-HEP), with average molecular weight of 7 kDa, and dermatan sulfate (SDX-DS), with average molecular weight of 25 kDa. Other possible components comprised in sulodexide are chondroitin, heparin sulfate. Sulodexide has to be considered as a unique active ingredient, different from other glycosaminoglycans, comprising about 80% in weight of SDX-HEP and about 20% in weight of SDX-DS. These components have not been isolated until now and the components of sulodexide are determined with analytical method as gel permeation chromatography and electrophoresis.

It is known that sulodexide shows high affinity for anti-thrombin III and for Heparin-cofactor II, inhibits the factor Xa and thrombin, activates tissular plasminogen and reduces the fibrinogen level as described by Ofosu F. A. in Semin. Thromb. Hemost. 24 (1998), 127-38 and by Ceriello A. et al. in Diab. Nutr. Metab., 6 (1993), 1-4.

Since, it is known that the plasmin activation from plasminogen is one of the local activation mechanism of MMPs, the known properties of sulodexide lead to conclude that this compound would have increased the concentration of circulating MMPs.

The present invention describes sulodexide or one of its components, in particular SDX-DS or SDX-HEP, to inhibit and/or reduce circulating MMPs, and in particular MMP-9, said also gelatinase B, involved in a number of diseases, in particular, an infection or a neoplastic disease, vascular disease characterized by a high level of MMPs, gastrointestinal ulcers, increase and progression of the tumor, growing of the primary tumor, altered angiogenesis, extravasation and intravasation of the neoplastic cells and combination thereof. As to vascular disease characterized by a high level of MMPs, the present invention, in particular relates to chronic venous insufficiency (CVI); varicose veins, cardiac break after myocardium infarct, abdominal aortic aneurysm, the venous relaxing, pulmonary pathology, and neoplastic pathologies.

Another unexpected and important aspect of the present invention is the dermatan sulfate (SDX-DS) and the low molecular weight heparin (SDX-HEP) isolated from sulodexide, the process to obtain them and their use to inhibit and/or reduce the release of MMPs in vitro and in vivo, alone or in their mixture.

This result is indeed unexpected, because in literature, for example in Cell Biol. Int. 2003, 27, 779-84, Isnard N. et al. describe that the dermatan sulfate activates the expression of MMP-2 and MMP-9.

The surprising characteristics of the SDX-DS, have been demonstrated comparing it with commercial dermatan sulfate, and results are shown in Examples 2-9.

This evidence makes sulodexide indeed a unique compound, different from any other glycosaminoglycans, which might be prepared with low molecular weight heparins and dermatan sulfates, available in the market, for the treatment of all pathologies wherein MMPs are involved.

Another aspect of the present invention is the SDX-DS isolated from sulodexide.

Another aspect of the present invention is the SDX-HEP isolated from sulodexide.

Another particular aspect of the present invention is the dermatan sulfate obtained from sulodexide through purification process, such as in affinity chromatography with AT III functionalized medium.

Another particular aspect of the present invention is the low molecular weight heparin obtained from sulodexide through purification process, such as in affinity chromatography with AT III functionalized medium.

Another aspect of the present invention are pharmaceutical compositions comprising SDX-DS or SDX-HEP and their use as medicine.

DESCRIPTION OF THE INVENTION

Object of the present invention are sulodexide, or one of its components, in particular SDX-DS, or SDX-HEP, isolated from sulodexide, and their use as medicament in all pathologies wherein MMPs are involved. In particular the invention describes the use of sulodexide, or SDX-DS, or SDX-HEP for reduction and/or inhibition of circulating MMPs, in particular the inducible form of gelatinase MMP-9 with consequent decrease of concentration of circulating MMPs in blood. The isolated components can be used for medicament either per se or in mixture thereof.

Sulodexide is present as medicine available in the market with trademark VESSEL 2 F®, and it is administrated by oral route, intramuscular or intravenous injection, for the treatment of vascular pathologies with thrombotic risk such as peripheral arterial disorder, post phlebitis syndrome, for treatment of albuminuria in nephropathies as described by Harenberg J. in Med. Res. Rev. 18 (1998), 1-20 e Tamarin R. in Medical Praxis 8 (1997), 1.

Sulodexide and its derivatives, in particular SDX-DS and SDX-HEP are also herein intended to comprise their pharmaceutically acceptable salts, solvates, hydrates, and clathrate.

An important aspect of the present inventions is the specificity of the sulodexide for the inhibition/reduction of MMP-9, called also gelatinase B, involved in the venous relaxing, varicose veins, chronic venous insufficiency (CVI) and ulcers of lower limbs.

Sulodexide or SDX-DS or SDX-HEP, can be used as active ingredient in all pathologies characterized by an increase of inducible MMP-9, without any effect on the constitutive MMP-2. An advantage of sulodexide or its components is the possibility to be administrated by oral or injective route, intramuscular or intravenous. Another advantage of sulodexide and its components is given by the possibility to administrate a high dosage without side effect as described in EP 1292315, is well tolerated up to 1000 mg/day and higher, The present invention describes a new use of sulodexide or SDX-DS or SDX-HEP for the reduction and/or inhibition of concentration of MMPs, in particular MMP-9 (Gelatinase B, EC3.4.24.35 di 92, 130 e 225 kDa).

The present invention describes sulodexide of one of its components, in particular SDX-DS and SDX-HEP for use in the inhibition or reduction of MMPs, in particular MMP-9, in a quantity of higher than 20%.

The present invention describes amounts of sulodexide or SDX-DS or SDX-HEP, sufficient to obtain a reduction and/or inhibition in the release of MMP-9 from blood cells into the plasma circulation with consequent decrease of the activity of circulating MMPs in venous apparatus and consequent reduction of enzymatic activity in situ in the vein walls. Such effect occurs in vitro and in ex-vivo sulodexide concentration in a range from 8 µg/ml to 12 µg/ml. These concentrations correspond to therapeutically acceptable dosages that can be reached in the blood through administration of sulodexide by intravenous, intramuscular or oral route at dosages comprised between 20 mg and up to 1000 mg/day. The effect of sulodexide, SDX-DS, SDX-HEP on MMPs at the described concentrations has been demonstrated with ex-vivo experiments on biological samples.

In detail, blood samples were collected from 50 health volunteers, male and female. The samples, manipulated to obtain the corresponding plasma and serum samples, were analyzed with or without the addition of variable concentration of sulodexide SDX-DS and SDX-HEP.

The invention describes also the SDX-DS comprised in the sulodexide, at a concentration of about 20% by weight, SDX- HEP at a concentration of about 80%, the process to obtain them, and the use as a medicament and for the treatment in all the pathologies wherein MMPs are involved. SDX-DS and SDX-HEP can be obtained with purification and extraction process.

In particular Example 1 describes the process for obtaining SDX-DS and SDX-HEP from sulodexide through affinity chromatography purification, wherein the heparin fraction is adsorbed to a stationary phase functionalized with AT III, and the dermatan fraction is collected in the non adsorbed flow through.

Example 2 describes the effect of the addition to whole blood of increasing sulodexide quantities to a final concentration of from about 10 μg/ml to about 50 μg/ml and SDX-DS, extracted from sulodexide, at a final concentration of from about 0 to about 10 μg/ml. After centrifugation, the serum from the whole blood samples have been collected and analyzed in gelatine-zymography, as described by Mannello F. et al. in Clin. Chem. 2003, 49, 339-34. In order to normalize the MMPs activities in different samples, the volume of samples was adjusted to the same quantities of the total proteins. The densitometric results of gelatin-zymography are showed in Table 2, wherein it has been assigned the value of 100% to the MMPs area of the samples of serum without the addition of sulodexide or of the MMPs inhibitor and calculated the reduction of the area of MMPs in the presence of sulodexide and SDX-DS. It has been observed that the area of the band corresponding to MMP-9 is reduced of at least about 20% at the sulodexide concentration corresponding to about 10 μg/ml and at less than one tenth with the sulodexide concentration corresponding to about 50 μg/ml.

MMP-2 concentration remains unaffected by the addiction of sulodexide.

It results that the addition of sulodexide to whole blood samples, to final concentration from about 10 μg/ml to about 50 μg/ml, reduces in the corresponding serum samples and in a proportional manner the circulating MMPs concentration, in particular of MMP-9, while the MMP-2 concentration remains unchanged.

Table 2 reports also the densitometric results of samples treated with SDX-DS, wherein the area of the band relative to MMP-9 is reduced of at least about 20% at the concentration corresponding to about 2.5 μg/ml and at least about 60% at the final concentration of about 10 μg/ml.

From these results it can be inferred that the effect of the reduction/inhibition of MMPs is favored by the presence of SDX-DS comprised in sulodexide and these results make sulodexide a unique active ingredient among glycosaminoglycans.

These data are also confirmed by quantitative Elisa analysis executed with kit Biotrak® MMPS Amersham, which recognizes proMMP of gelatinase with limit of detection (LOD) corresponding to 0.37-0.25 μg/ml.

Table 3 confirms that sulodexide at a concentration of about 25 μg/ml reduces of at least about 20% the area of the band relative to MMP-9 and of at least about 60% with a concentration of about 50 μg/ml. The addition of SDX-DS as obtained in Example 1, reduces the MMPs in a quantities of at least about 20% at a concentration of about 2.5 μg/ml and of at least about 60% with a concentration of about 10 μg/ml.

The demonstration that sulodexide also acts on the reduction of the release of MMPs by platelets and leucocytes, is evident in Example 3, in which sulodexide is added to plasma samples, after having removed the cellular component of the whole blood with centrifugation.

Example 3, reports the results relative to the addition of sulodexide to the blood samples, collected from 50 healthy volunteers, average age of 37, previously treated with a 0.13 M sodium citrate solution, in an amount between 1 and 10% by volume, and then centrifuged. To the sample supernatants, sulodexide quantities were added to final concentration of from about 10 μg/ml to 50 μg/ml. The samples were analyzed by gelatin zymography as described in Example 2.

It has been assigned a value corresponding to 100% to the band of the serum sample without any addition, (control), and determined the proportional area reductions in function of increasing sulodexide quantities to the serum samples. It has been observed that the clear bands of gelatine digestion relative to MMP-9 proteolytic activity remain unchanged after the addition of sulodexide, as reported in Table 4 of Example 3, and this result demonstrates that sulodexide does not interfere with the MMPs activity once the enzymes are already released in the plasma.

A similar result is obtained when sulodexide is added to serum samples as reported in Example 4, in which increasing quantities of sulodexide were added. In particular, Example 4, describes the effect of increased quantities of sulodexide from about 10 μg/ml to about 50 μg/ml, added to serum samples, obtained after centrifugation of blood sample collected from 50 healthy volunteers, average age of 37. The obtained sera samples were analyzed in zymography as described in Example 2.

The relative densitometric value of gelatinolytic areas correlated to MMP-2 and MMP-9 gelatinolytic bands are reported in Table 5, wherein no reduction is observed in respect to the bands of the sample without addition of sulodexide.

In particular, the obtained results from Example 2, demonstrate that sulodexide and SDX-DS, comprised in sulodexide, prevent the increase and reduce MMPs in the blood, through a mechanism of action, which acts selectively on the inducible form of MMP-9, identifying a possible therapeutic use for the treatment of all pathologies wherein the presence of MMP-9 is directly or indirectly correlated with the course of the disease.

Example 5 reports the comparison between sulodexide, parnaparin and SDX-DS, extracted from sulodexide, on the MMPs present in the serum. Whole blood samples, collected from healthy volunteers, were treated as in Example 2, a group of samples were treated with sulodexide to a final concentration of about 25 μg/ml, a group with dermatan sulfate to a final concentration of about 5 μg/ml and a group with a low molecular weight heparin (parnaparin) to a final concentration of about 20 μg/ml. Table 8 and Table 9 report the obtained results in zymography and Elisa respectively, wherein sulodexide shows an MMP-9 reduction of from 50% to 70%, parnaparin from about 20% to 30% and SDX-DS from about 50% to 70%, in respect to the control sample without any addition.

The unique property of sulodexide in the release of MMPs has to be attributed to the natural mixture of GAGs which constitute sulodexide.

Example 6 provides support the characteristics of SDX-DS in the reduction of MMPs, in comparison with two different dermatan sulfates commercially available in the market. At the same concentration of 5 μg/ml, SDX-DS induces an MMP-9 reduction of higher than 50%, while the two commercial dermatan sulfates (Sigma and Calbiochem) induce a reduction of less than 10%.

It has been found that SDX-DS reduces MMPs, and in particular MMP-9, at least three times more than the commercial DS preparations.

Example 7 demonstrate that also the SDX-HEP has unique features, in fact the mixture of low molecular weight heparin and dermatan sulfate comprised in sulodexide, act differently in respect to the synthetic mixture prepared adding parnaparin to commercial dermatan sulfate and SDX-DS;

In more detail, sulodexide is compared with mixtures of low molecular weight heparin and dermatan sulfates mixed in about the same ratio present into sulodexide of about 80% parnaparin and of about 20% dermatan sulfate. The data reported in Table 11, indicate that sulodexide show significantly higher percentage of inhibition in respect to the parnaparin/DS and parnaparin/SDX-DS mixtures.

In particular the observation that sulodexide has a superior activity in respect to the mixture heparin/SDX-DS let to demonstrate that the heparin component comprised in sulodexide has also unique properties affecting the level of circulating MMPs.

The capacity of sulodexide in respect to MMPs on biological sample as inner wall of veins has been also demonstrated.

The inner walls of veins are particularly important because this is the site of action of MMPs, causing several pathologies related to the proteolytic remodeling of the extracellular matrix.

Example 8 shows the comparative effect of sulodexide, SDX-DS and parnaparin on MMPs on the venous walls in immunohistochemistry experiment. This experiment confirms the effect of sulodexide and SDX-DS in all the pathologies wherein MMPs are involved and in particular in the reduction and/or inhibition of concentration of MMPs expression. Sulodexide, SDX-DS and parnaparin at concentration respectively of about 25, 5 and 20 µg/ml were added to human saphenous vein segments, surgically obtained from 10 healthy women (age mean 42 years), undergoing to saphenectomy for varicose vein.

After appropriate tissue inclusion, serial sections of about 5 µm of thickness were incubated with a monoclonal antibody anti MMP-9 and after incubation with a biotinylated secondary antibody, the complex was detected by peroxidase reaction according to the standard methods. The complex after incubation was detected by with avidin-peroxidase, according to the standard methods.

The tissue samples treated with sulodexide showed reduced surfaces of the stained area, demonstrating a lower local concentration of MMPs, in respect to the control and heparin treated samples.

Table 12 demonstrates that, assigning a value corresponding to 100 to the sample without any addition, sulodexide at a concentration of about 25 µg/ml reduces the intensity of stain area of MMP-9, corresponding to about 60%; SDX-DS at a concentration of about 5 µg/ml reduces the intensity of to about 70% and parnaparin at concentration of about 20 µg/ml does not reduces the intensity of MMP-9. These in vitro results of sulodexide and SDX-DS in vitro are transferable to in vivo use and applicable to the reduction of MMPs in all pathologies wherein they are involved.

Example 9 shows the effect of sulodexide, SDX-DS and parnaparin on MMPs on the venous walls by in situ zymography (cytochemistry).

Sulodexide, SDX-DS and parnaparin at a concentration respectively of about 25, 5 and 20 µg/ml were added to human saphenous vein segments, surgically obtained from 10 healthy women (age mean 42 years), undergoing to saphenectomy for varicose vein.

After, the treatment the vein sections were incubated with a fluorogenic gelatine substrate and the proteolytic activity observed by comparing the microscope image of venous portions at 530 nm.

In these experiments, the level of fluorescence is proportional to the MMPs activities on the tissue and the results in situ zymography are reported Table 13.

Table 13 demonstrates that, assigning a value corresponding to 100 to the sample without any addition, sulodexide at a concentration of about 25 µg/ml reduces the intensity of MMP-9 to about 50%; SDX-DS at a concentration of about 5 µg/ml reduces the intensity of MMP-9 to about 80% and parnaparin at concentration of about 20 µg/ml reduces the intensity MMP-9 to about 40%.

The effect of sulodexide, SDX-DS, and SDX-HEP on the vein tissue for the reduction and/or inhibition can be extended to all the tissues wherein the MMPs are involved.

For example sulodexide, SDX-DS and SDX-HEP can also be used in the treatment of intestinal ulcer and other damage imputable to MMPs without any limitation.

In order to obtain the in vivo efficacy concentrations in the reduction of MMPs and in particular MMP-9, sulodexide may be administered by intravenous route, injecting from 1 to 4 vials of solution containing about 60 mg/ml sulodexide with pharmaceutical acceptable excipients. Alternatively sulodexide may be administered at dosage therapeutically equivalent dosage by intramuscular or oral route. In this latter case it is possible to administer up to 1000 mg/day and higher dosages, without any adverse events, as described in EP 1292315.

The property of sulodexide in the reduction of circulating MMPs and especially the selective action against MMP-9, is an unknown and unexpected effect, in particular useful in all the pathologies wherein MMPs are involved, and in particular MMP-9, such as vascular disease, chronic venous insufficiency (CVI), varicose veins, venous ulcers, pulmonary pathologies, increase and progression of the tumor, growing in the primary tumor, angiogenesis, extravasations and intravasation of neoplastic cells.

The reported and not limiting experiments, demonstrate a new use of sulodexide, SDX-DS and heparin fraction of sulodexide, for the reduction/inhibition of release of MMPs, in particular MMP-9, released by leucocytes and platelets and the inhibition of the values of MMP in the inner walls of veins. The ex-vivo results are completely transferable to the use of sulodexide SDX-DS and heparin fraction of sulodexide in vivo by means of a pharmaceutical composition comprising sulodexide from about 20 to 1000 mg and higher; SDX-DS from about 4 mg to about 200 mg and higher; SDX-HEP form about 16 to about 700 and higher.

Moreover, sulodexide, SDX-DS and SDX-HEP, administration can occur by injective route, intramuscular and/or intravenous or oral route, without any limitation.

The dosage of active ingredient, sulodexide, SDX-DS and SDX-HEP, can vary considerably depending on the mode of administration, the patient's age, weight and the patient's general condition, as well the severity of the disease, and can be determined by standard techniques. In additional, in vitro and animal assay may optionally be employed to help to identify optional dosage ranges. Preferably the pharmaceutical composition is in a form acceptable for oral administration. Sulodexide, SDX-DS and heparin fraction of sulodexide, in the present invention can be comprised in a composition in the form of tablets, capsules, granulates, suspensions, solutions or aerosol.

Oral pharmaceutical composition can provide controlled release.

Oral pharmaceutical composition can provide bioadhesive properties to increase mucoahesivity.

Excipients for oral preparation are selected among one or more ligants, glidants, disintegrants, diluents, natural agents.

The excipients for oral use can comprise disintegrants, diluents, and combination thereof. Disintegrants can be selected from crospovidone, sodium starch glycolate, corn starch, cellulose derivatives and combination thereof. Diluents can be selected from lactose, mannitol, xylitol, microcrystalline cellulose, sugar, dextrin, hydrophilic carbohydrate, and combination thereof. Oral pharmaceutical form can comprise biohadesive excipients.

Tablets can further comprise a coating, which comprises hydroxypropyl methylcellulose, hydroxymethyl cellulose, polyvinyl-pyrrolidone, polyethylene glycol, dextrin, maltodextrin, polyvinyl acetate based compounds, hydroxypropyl cellulose, cellulose acetate, cellulosephtalate, derivative thereof, or combination thereof.

Oral form can also comprise flavoring, coloring or sweetener agents.

Pharmaceutical compositions comprising sulodexide or SDX-DS and SDX-HEP in respect to the known and studied compounds for the reduction/inhibition of controlled release of MMPs, provide many advantages and solve many problems such as the specific selectivity in respect to MMP-9, tolerability, safety and acceptability.

This invention refers to a new therapeutic use different in respect to the ones for sulodexide is marketed in the prevention of vascular pathologies with thrombotic risk.

In the pharmaceutical practice, sulodexide, SDX-DS and SDX-HEP can be combined with acceptable excipients using the conventional techniques known to the skilled person.

The composition can be administered in single or multiple dosage, one or more times in a day in controlled release composition.

Prior art describes the use of sulodexide in pathologies related to the diabetes, such as diabetic nephropathy, while only now, after the present invention it is possible to have a new medical use for sulodexide.

Object of the present invention are also pharmaceutical compositions comprising SDX-DS and SDX-HEP useful in the treatment of all pathologies wherein MMPs, in particular MMP-9, are involved, without any limitation.

A particular aspect of the present invention is the above use for treatment of pathologies wherein venous relaxing is involved, for example varicose vein formation, chronic venous insufficiency; gastrointestinal ulcers, pulmonary pathologies, and neoplastic pathologies.

Another particular and important aspect of the present invention is SDX-DS isolated from sulodexide and its use to inhibit and/or reduce the release of MMPs in vitro and in vivo.

Another aspect of the invention is SDX-DS obtained by sulodexide with a purification process.

Another particular aspect is SDX-DS with affinity chromatography with a column functionalized with AT III.

The process for the isolation of SDX-DS comprises the following steps:

a) preparation of affinity chromatographic column with ATIII at a concentration between 5 and 10 mg/ml gel;

b) loading sulodexide in said column of step a) at a concentration comprised between 0.1 to 5 mg/ml gel in a buffer comprising TRIS 50 mM, Na Cl 50 mM, at pH 7.4;

c) pooling eluted dermatan sulfate fractions in non absorbed fraction and optionally lyophilize said pooled dermatan sulfate;

d) optionally transforming said dermatan sulfate in a pharmaceutically acceptable salt, solvate, hydrate, clathrate thereof.

Another aspect of the invention is SDX-HEP obtained by sulodexide with a purification process.

Another particular aspect is SDX-HEP with affinity chromatography with a column functionalized with AT III.

The process for the isolation of SDX-HEP comprises the following steps:

a) preparation of affinity chromatographic column with ATIII at a concentration between 5 and 10 mg/ml gel;

b) loading sulodexide at a concentration comprised between 0.1 and 5 mg/ml gel in a buffer solution comprising TRIS 50 mM, NaCl 50 mM at pH 7.4;

c) eluting low molecular weight heparin from said chromatography column with a buffer solution comprising TRIS 50 mM, NaCl 3 M at pH 7.4;

d) pooling the eluted low molecular weight heparin fraction and optionally lyophilize said pooled heparin;

e) optionally transforming said low molecular weight in a pharmaceutically acceptable salt, solvate, hydrate, clathrate thereof.

Another particular and important aspect of the present invention is SDX-HEP and its use to inhibit and/or reduce the release of MMPs in vitro and in vivo.

Another aspect are pharmaceutical compositions comprising sulodexide, in solid form, suspension, granule, aerosol for the treatment of pathologies wherein MMPs are involved and need to be reduced.

Another aspect are kits comprising pharmaceutical composition comprising sulodexide, SDX-DS and SDX-HEP.

Another aspect is the use of pharmaceutical compositions comprising sulodexide or one of its components, in particular SDX-DS or SDX-HEP or a mixture thereof, in a dosage suitable for the administration of at least about 5 mg/day. Examples of daily dosages are from 5 to 1000 mg/day, from 15 to 800 mg/day, from 50 to 200 mg/day, from 20 to 1000 mg/day or higher, in one or more administration, without any limitation.

A preferred daily dosage for SDX-DS is from 1 to 300 mg or higher in particular from 4 to 300 mg in single or multiple administration without any limitation.

A preferred daily dosage for SDX-HEP is from 16 to 900 mg or higher mg in particular from 19 to 800 mg, in single or multiple administration without any limitation.

Pharmaceutical composition comprising sulodexide, SDX-DS and SDX-HEP can be administered to patients who receive concomitant therapies, without any negative effect.

The use of sulodexide, SDX-DS and SDX-HEP, described in the present invention, have to be considered a new medical use for the treatment of all pathologies wherein MMPs are involved and it is requested their reduction and/or inhibition. The use of sulodexide, SDX-DS and heparin fraction of sulodexide, in comparison with previous studied compounds in the art, overcomes several and important problems such as the specific selectivity for MMP-9, the compliance and the easily administration.

The invention is showed in details in the following examples, which have not to be considered as limiting of this invention.

EXAMPLE 1

Process to Obtain Dermatan Sulfate Fraction from Sulodexide

A quantity of sulodexide extracted from intestinal animal mucosa, corresponding to 8 mg was dissolved in a binding buffer constituted by TRIS 50 mM and NaCl 50 mM at pH 7.4, and loaded on an affinity column prepared by coupling 7.5 mg of ATIII/ml of CNBr-activated Sepharose gel (GE).

The column was washed with the same buffer solution and the absorbed material was eluted with a buffer solution consisting of TRIS 50 mM, NaCl 3M at pH 7.4.

Dermatan sulfate fraction was collected in the non absorbed material present in the flow-through, while heparin fraction, is collected in the eluted fractions.

Dermatan sulfate and heparin fraction could be stored at −20° or optionally lyophilized.

Heparin pooled fractions and dermatan sulfate pooled fractions were analyzed in gel permeation chromatography (GPC) and in agarose gel.

Chromatographic profiles were obtained in HPLC system HP 1090, equipped with GPC column TSK gel, G2000 SWXL (7.8×300 mm) eluted with $Na_2SO_4$ 0.2 M, pH 5 at flow rate corresponding to 0.2 ml/min and detected with Refraction Index detector.

Figure 1:
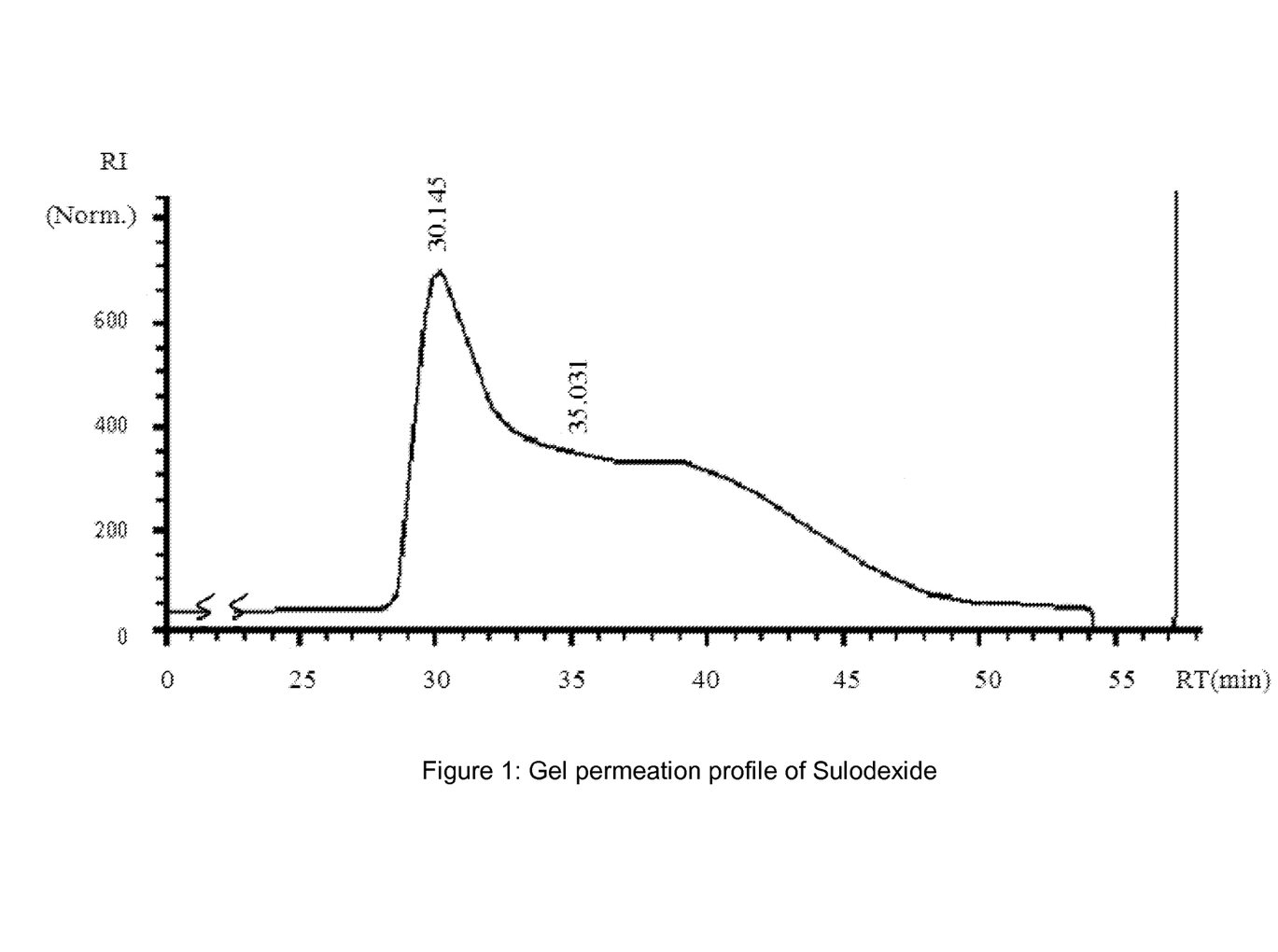
FIG. 1: Gel permeation profile of sulodexide.

FIG. 1 shows the chromatographic profiles of sulodexide loaded in affinity chromatography with a broad chromatographic GPC profile with a maximum sharp peak at RT corresponding to about 30 min.

Figure 2:
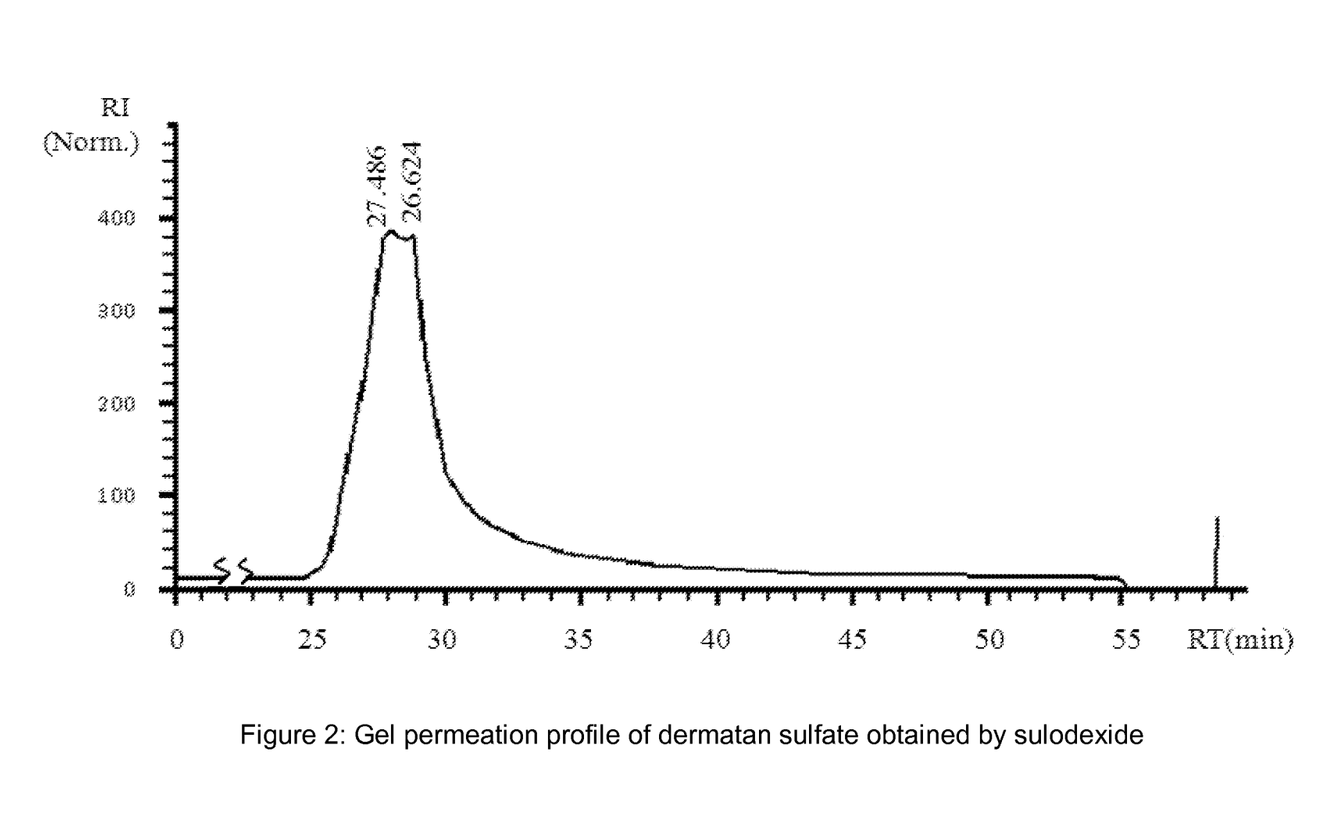
FIG. 2: Gel permeation profile of dermatan sulfate obtained by sulodexide.

FIG. 2 shows dermatan sulfate fraction present in the flow-through of affinity chromatography with a shorter peak with maximum at RT about 27 min.

Figure 3:
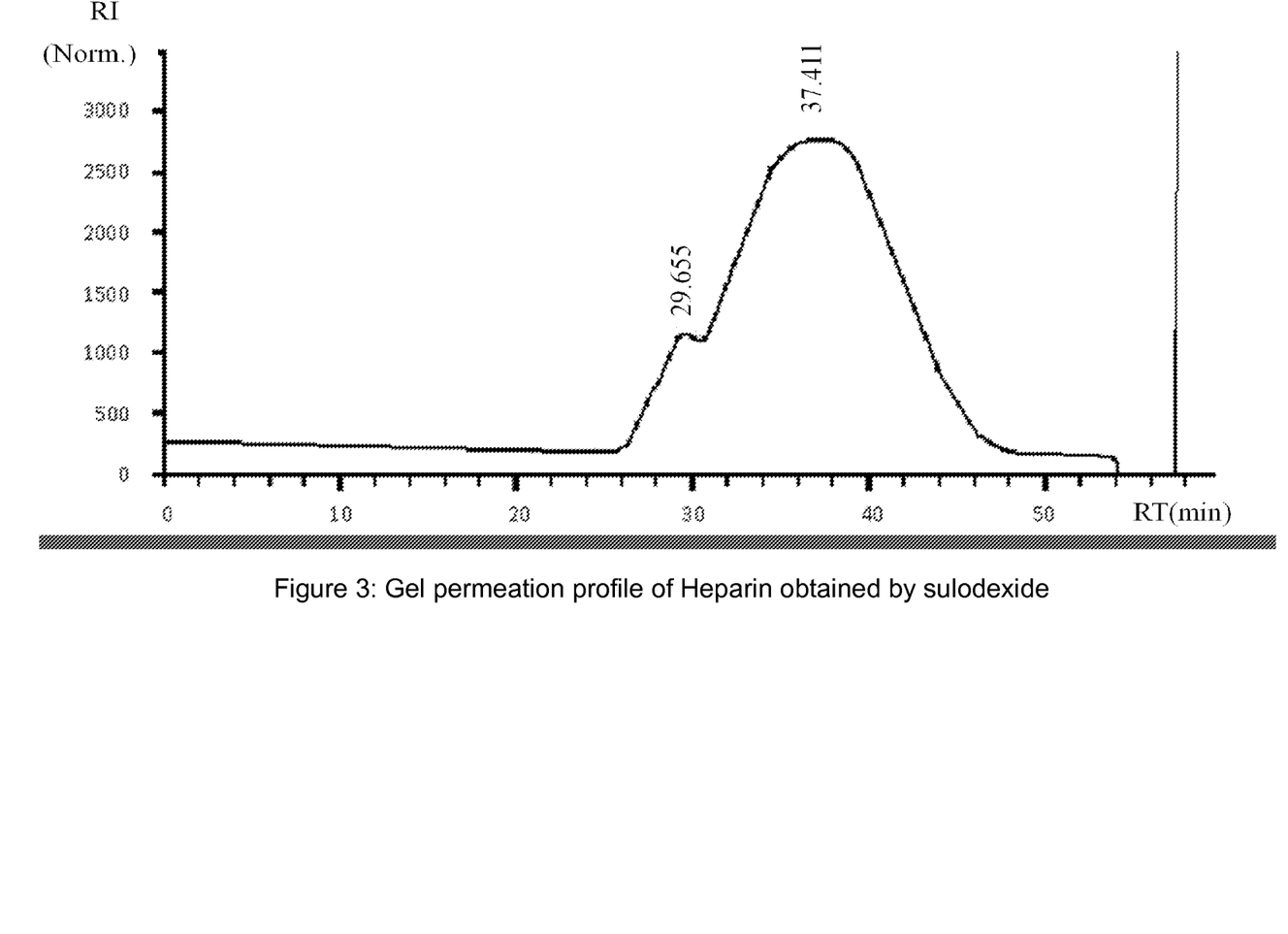
FIG. 3: Gel permeation profile of heparin obtained by sulodexide.

FIG. 3 shows heparin fraction eluted by affinity chromatography characterized by a broad peak.

Agarose gel analysis was obtained dissolving agarose at a concentration of 0.6% (w/v) in Barium Acetate Buffer 0.04 M pH 5.8. The warm solution was placed on a glass plate with dimensions of about 7.5 cm×4.5 cm and sulodexide, SDX-DS and SDX-HEP at concentration of about 10 mg/ml, comprising a little quantity of stain Cresol Red, were loaded in the agarose gel. Electrophoretic separation was carried out in two steps: the first step in barium acetate buffer 0.04 M pH 5.8, at 100 V for about 25 min and the second step in 1,3-diamminopropane 0.05 M, pH 9 at 110 V for about 30-40 minutes. The plate was then plunged in the fixing solution consisting of cetylpyridinium chloride 0.1% (w/v) in water for about 3 hours. After drying the plate under warm air, the plate was plunged in the staining solution consisting of Tolnidine Blue 0.1% (w/v) in ethanol/water/acetic acid 50:50:1 (v/v/v) destained in the same solution without stain and dried under warm air.

The relative mobility (Rf) of sulodexide, its separated components SDX-DS and SDX-HEP and commercial dermatan sulfate are reported in Table 1.

TABLE 1

| Component (μg/ml) | Rf |
| --- | --- |
| Sulodexide | 0.86 |
| | 0.75 |
| Dermatan sulfate fraction (SDX-DS) | 0.84 |
| Heparin Fraction (SDX-DS) | 0.75 |
| Commercial Dermatan sulphate (Sigma) | 0.86 |

EXAMPLE 2

Effect of Sulodexide on Circulating MMPs in Blood Samples

Samples of blood collected from 50 healthy volunteers, 25 female and 25 male of age between 25 and 58, average age of 37 years, were placed in test tubes and two sets of samples were prepared; in the first set were added variable amount of sulodexide until to obtain final concentration corresponding to 0, 12, 24, 48 μg/ml, in the second set were added variable amounts of dermatan obtained as in Example 1, up to the final concentration corresponding to 0, 2.5, 5, and 10 μg/ml. The samples without the addition of sulodexide and dermatan were used as control and the bands of MMPs, of these samples were attributed the arbitrary value of intensity of 100%. The intensity of the MMPs bands of the treated samples were reported as percentage in respect to the untreated samples.

Overall samples were centrifuged at 1550 g for 10 minutes at 4° C., an amount of supernatants of serum samples (S) corresponding to 150 μg of total proteins, determined by Bradford method, was analyzed by zymography-gelatin. The samples were loaded in gel zymography and the electrophoresis separation was compared with standard of MMPs, prepared diluting the capillary blood from healthy volunteers by 15 volumes of Laemmli U.K buffer (Nature, 227 (1970), 680-685), in non reducing conditions.

The zymograms in gelatin were prepared by polyacrylamide at 7.5% (p/v) containing 0.2% (p/v) gelatin isolated by swine cute (Type A 90 Bloom, Sigma).

The electrophoresis was carried out at 35 mA for 75 minutes, the gels were washed with Triton X-100 solutions at concentration of 2.5% (v/v) and incubated for 24 hours at 37° C. in a solution constituted by 50 mM Tris-HCl, pH 7.5, 5 mM $CaCl_2$, 100 mM NaCl, 1 mM $ZnCl_2$, 0.3 mM $NaN_3$, 0.02% (p/v) of detergent Brij®-35 e 0.25% (v/v) di Triton X-100. The detection of gelatinase activity in situ, occurs by staining the gels with Coomassie Brilliant blue R-250 at a concentration of 0.2% (p/v) and subsequently bleaching with a solution of methanol-acetic acid in a volumetric ratio equal to 80/20.

Sulodexide and SDX-DS, obtained as in Example 1, acts only on the band relative to MMP-9, while the intensity of the band of MMP-2 remains unchanged in respect to the control and a value 100% is attributed. The calculation of the areas was executed with a densitometer with imagine analyzer. In Table 1 are reported the percentage areas of gelatinolytic digestion related to MMP-9 in serum samples with or without sulodexide, with or without dermatan fraction.

TABLE 2

Gelatin-Zymography: Concentrations of serum MMP-9 after treatment with sulodexide and dermatan sulfate obtained as in Example 1

| Sulodexide (μg/ml) | Area % MMP-9 | Dermatan sulphate obtained by Example 1 (μg/ml) | Area % MMP-9 |
| --- | --- | --- | --- |
| 0 | 100 ± 7 | 0 | 100 ± 7 |
| 12 | 57 ± 4 | 2.5 | 46 ± 3 |
| 24 | 41 ± 5 | 5 | 30 ± 7 |
| 48 | 7 ± 1 | 10 | 4 ± 7 |

The concentrations of MMP-9 in the samples are determined also in Elisa, for the measurements of enzymatic activity of metalloproteinase, using the Biotrak MMPs assay, Amersham, which recognized the forms pro-MMP of gelatinase with a LOD of 0.37-0.25 µg/L for MMP-9 and MMP-2, the results obtained are reported in Table 2. The Elisa results do not show statistically significant differences from the activity gelatinolytic seen in zymographies.

TABLE 3

Elisa Assay: Concentration of serum MMP after treatment with sulodexide and dermatan sulfate obtained as in Example 1

| Sulodexide (µg/ml) | % MMP-9 | Dermatan sulphate obtained by Example 1 | % MMP-9 |
|---|---|---|---|
| 0 | 100 ± 4 | 0 | 100 ± 4 |
| 12 | 61 ± 6 | 2.5 | 47 ± 4 |
| 24 | 43 ± 8 | 5 | 31 ± 5 |
| 48 | 6 ± 3 | 10 | 5 ± 1 |

EXAMPLE 3

Effect of Sulodexide on the Amounts of Circulating MMPs in the Plasma

Samples of blood are collected from 50 healthy volunteers, 25 female and 25 male of age between 25 and 58, average age of 37, and 1 ml of each sample is added to 38 µl of a solution of sodium citrate 0.13 M and centrifuged at 1550 g for 10 minutes at 4° C.

Increased amounts of sulodexide are added to the samples up to obtain final concentration corresponding respectively to 0, 12, 24 and 48 µg/ml.

An amount corresponding to 150 µg of total proteins of supernatants of plasma samples (P) obtained by centrifugation, measured through Bradford method, is analyzed by zymography-gelatin. The standard of gelatinase, prepared diluting the capillary blood from healthy volunteers by 15 volumes of Laemmli buffer, in non reducing conditions, are loaded in the gel.

The gelatin-zymograms and the electrophoresis rune are executed as described in Example 2.

The zymograms areas of the band are determined using a densitometer with imagine analyzer, calculating the increase of the area of the bands relative to metalloproteinase in comparison with those of the plasma without addition of sulodexide. The percentage areas of gelatinolytic digestion relative to MMP-9 in sample of blood with or without sulodexide are reported in Table 4.

TABLE 4

Gelatin-zymography: Concentration of plasmatic MMP-9 after treatment with sulodexide

| Concentration of sulodexide (µg/ml) | Area % MMP-9 |
|---|---|
| 0 | 100 ± 5 |
| 12 | 98 ± 4 |
| 24 | 101 ± 4 |
| 48 | 99 ± 4 |

The densitometric analysis of MMP-9 of zymogram is confirmed by quantitative analysis of Elisa, whose data, reported in Table 4, do not show significant differences in comparison with densitometric analysis of zymogram.

TABLE 5

Elisa assay: Concentration of plasmatic MMP after treatment with sulodexide

| Concentration of sulodexide (µg/ml) | Concentration % MMP |
|---|---|
| 0 | 100 ± 7 |
| 12 | 99 ± 5 |
| 24 | 100 ± 3 |
| 48 | 98 ± 4 |

EXAMPLE 4

Effect of Sulodexide on the Amounts of Serum Circulating MMP, after Serum Formation Samples of blood collected from 50 healthy volunteers, 25 female and 25 male of age between 25 and 58, average age of 37, are placed in test tube and centrifuged at 1500 g for ten minutes at 4° C.

Growing amounts of sulodexide are added to 150 µg of proteins of serum, measured by Bradford method, to obtain final concentration of sulodexide corresponding respectively to 0, 12, 24, 48 µg/ml. The samples obtained are analyzed through zymography-gelatin in comparison with standard of gelatinase, prepared diluting the capillary blood from healthy volunteers by 15 volumes of Laemmli buffer, in non reducing conditions.

The zymograms, the electrophoresis course and the coloration/decoloration are executed as described in Example 2.

The zymograms areas of the band are determined using a densitometer with imagine analyzer, calculating the decrease of the area of the bands relative to metalloproteinase in comparison with those of the serum without addition of sulodexide. The percentage areas of gelatinolytic digestion relative to MMP in sample of serum with or without sulodexide are reported in Table 6.

TABLE 6

Gelatin-zymography: Concentrations of serum MMP-9 in presence of growing concentrations of sulodexide

| Concentrations of sulodexide (µg/ml) | Area (%) MMP-9 |
|---|---|
| 0 | 100 ± 6 |
| 12 | 98 ± 4 |
| 24 | 101 ± 3 |
| 48 | 99 ± 4 |

The data obtained by zymography, do not show significant differences in comparison with those obtained by Elisa, as reported in Table 7.

TABLE 7

ElisaAssay: Concentrations of plasmatic MMP with different concentrations of sulodexide

| Concentrations of sulodexide (µg/ml) | Concentration % MMP-9 |
|---|---|
| 0 | 100 ± 5 |
| 12 | 99 ± 2 |
| 24 | 101 ± 4 |
| 48 | 97 ± 6 |

EXAMPLE 5

Comparative Example

Evaluation of Sulodexide, Dermatan Sulphate Obtained by Example 1 and Parnaparin Blood sample prepared as described in Example 2 were divided in three groups wherein one group was treated with sulodexide at final concentration corresponding to 24 μg/ml, one group with parnaparin at final concentration corresponding to 5 μg/ml and the last group with dermatanic fraction obtained by Example 1 at concentration of 5 μg/ml, and compared in zymography and Elisa.

Results are reported in Table 8 and Table 9.

TABLE 8

Comparisons serum samples analyzed in zymography

| Sulodexide (μg/ml) | % MMP-9 | Parnaparin (μg/ml) | % MMP-9 | Dermatan Sulphate Example 1 (μg/ml) | Area % MMP-9 |
|---|---|---|---|---|---|
| 0 | 100 ± 7 | 0 | 100 ± 7 | 0 | 100 ± 7 |
| 24 | 41 ± 5 | 19 | 69 ± 7 | 5 | 30 ± 6 |

TABLE 9

Comparisons serum samples analyzed in Elisa

| Sulodexide (μg/ml) | % MMP-9 | Parnaparin (μg/ml) | % MMP-9 | Dermatan Sulphate Example 1 (μg/ml) | Area % MMP-9 |
|---|---|---|---|---|---|
| 0 | 100 ± 7 | 0 | 100 ± 7 | 0 | 100 ± 7 |
| 24 | 43 ± 8 | 19 | 67 ± 9 | 5 | 32 ± 8 |

These Examples confirm the effect of sulodexide and of the dermatan sulphate fraction present in sulodexide to reduce and/or inhibit the MMP and in particular MMP 9.

EXAMPLE 6

Comparative Example

Comparison Between Commercial Dermatan Sulfate and Dermatan Sulfate Obtained by Example 1

Blood sample prepared as described in Example 2 were divided in three groups wherein first group was treated with commercial dermatan sulfate commercialized by Sigma Aldrich (Italy); the second group with dermatan sulfate commercialized by Calbiochem (Italy) and the third with DS extracted by sulodexide as in Example 1, all at final concentration corresponding to 5 μg/ml. The samples were analyzed in Elisa as in Example 2, and the final results reported in Table 10.

TABLE 10

| Dermatan sulfate (Sigma Aldrich) (μg/ml) | % MMP-9 | Dermatan sulfate Calbiochem (μg/ml) | % MMP-9 | Dermatan Sulfate of Example 1 (μg/ml) | Area % MMP-9 |
|---|---|---|---|---|---|
| 0 | 100 ± 5 | 0 | 100 ± 5 | 0 | 100 ± 7 |
| 5 | 89 ± 8 | 5 | 95 ± 7 | 5 | 32 ± 8 |

EXAMPLE 7

Comparative Example

Comparison Between Commercial Dermatan Sulfate and Dermatan Sulfate Obtained by Example 1

Blood sample prepared as described in Example 2 were divided in five groups:

Group 1: blood sample with commercial parnaparin at concentration of 19 μg/ml;

Group 2: blood sample with sulodexide at concentration of 24 μg/ml;

Group 3: blood sample with DS obtained by sulodexide as in Example 1 at concentration of 5 μg/ml;

Group 4: blood sample with mixture of parnaparin at concentration of 19 μg/ml and DS obtained by sulodexide as in Example 1 at concentration of 5 μg/ml;

Group 5: blood sample with mixture of parnaparin at concentration of 19 μg/ml and commercial DS at concentration of 5 μg/ml.

The samples were analyzed in Elisa as described in Example 2 and the results reported in Table 11.

The reduction of MMP-9 was calculated in respect to the samples without any addition, who was assigned values area corresponding to 100%.

TABLE 11

Commercial DS Sigma and Calbiochem showed the same results.

| Composition | Concentration (μg/ml) | Area % MMP-9 |
|---|---|---|
| Sulodexide | 24 | 43 ± 8 |
| SDX-DS | 5 | 31 ± 6 |
| Parnaparin | 19 | 73 ± 9 |
| Parnaparin + SDX-DS | 19 + 5 | 55 ± 4 |
| Parnaparin + DS-Sigma | 19 + 5 | 87 ± 6 |

EXAMPLE 8

Ex-Vivo Evaluation of Sulodexide, Dermatan Sulphate (SDX-DS) and Parnaparin in Venous Walls in Immunophistochemistry Human saphenous vein segments, surgically obtained from 10 healthy women (age mean 42 years) undergoing to saphenectomy for varicose veins, were maintained under sterile condition in $CO_2$ incubator (5% $CO_2$ at 37° C. for 24 hours) in NaCl 0.9% and divided into three portions. The first portion was treated with sulodexide at concentration of 24 μg/ml; the second portion was treated with parnaparin at concentration of 19 ug/ml and the third portion with SDX-DS obtained by Example 1 at concentration of 5 μg/ml. The vein segments were fixed in 10% formalin solution, processed and embedded in paraffin wax. The finished embedded blocks were orthogonally oriented in respect to the original direction of blood flow, transverse 5 mm thick sections were then cut and mounted on 3-aminopropyl-triethoxysilane-coated slides. Portion of venous wall were cut into serial sections of 5 μm of thickness. Serial sections were examined by Miller's elastic van Gieson and Harris' haematoxylin and eosin staining. The sections were submitted to protein blockage with normal goat serum and then overnight incubated at 4° C., with a primary monoclonal antibody anti-MMP-9 (Santa Cruz) diluted 1:50 in phosphate buffered saline (PBS).

Vein sections were subsequently incubated with a secondary antibody (goat anti-mouse IgG biotinylated) as the standard methods and an avidin biotin peroxidase complex used.

After washing with PBS the vein sections were stain with DAB solution and $H_2O_2$ according to the standard method.

Subsequently, the sections were counterstained with Mayer's hematoxylin, dehydrated, cleared and mounted. Positive and negative controls were always included with each batch of staining to ensure consistency between consecutive runs.

The images were obtained with electronic microscope (40×) and the results summarized in Table 12. The intensity of the color was measured by optical inspection, assigned a value 100 to the tissue without any addition (control) and evalued the visible reduction of black color determined by the addiction of SDX-DS, SDX-HEP and parnaparin. The values are reported in Table 12.

TABLE 12

| | Concentration (μg/ml) | Reduction of Intensity % |
|---|---|---|
| Sulodexide | 24 | 60 |
| SDX-DS | 5 | 70 |
| Parnaparin | 19 | 0 |

EXAMPLE 9

Ex-Vivo Evaluation of Sulodexide, Dermatan Sulphate and Parnaparin in Venous Walls in In Situ Zymocgraphy (Cytochemistry)

Human saphenous vein segments, surgically obtained from 10 healthy women (age mean 42 years) undergoing to saphenectomy for varicose veins, were maintained under sterile condition in $CO_2$ incubator (5% $CO_2$ at 37° C. for 24 hours) in NaCl 0.9% and divided into three portions. The first portion was treated with sulodexide at concentration of 24 μg/ml; the second portion was treated with parnaparin at concentration of 19 ug/ml and the third portion with SDX-DS obtained by Example 1 at concentration of 5 μg/ml. The vein segments were fixed in 10% formalin solution, processed and embedded in paraffin wax. The finished embedded blocks were orthogonally oriented in respect to the original direction of blood flow, transverse 5 mm thick sections were then cut and mounted on 3-aminopropyl-triethoxysilane-coated slides. Segments of venous wall were cut into serial sections of 5 μm of thickness.

Vessel sections were incubated at 37° C. for 5 hours with a fluorogenic gelatin substrate (DQ Gelatin, Molecular probes) at concentration of 25 μg/ml in buffer constituted by 50 mM Tris-HCl, pH 7.5; 5 mM $CaCl_2$; 100 mM NaCl; 1 mM $ZnCl_2$; 0.3 mM $NaN_3$.

The proteolytic activities were observed in situ comparing the venous segments at 530 nm, and identifying them as green fluorescence. The densitometric analysis of situ zymography, in vein tissue, through cytochemical stain of MMP-9 of fluorogenic gelatin in the presence of SDX-DS, SDS-HEP and parnaparin in respect to the control and the data are reported in Table 13. A value 100 was assigned to the tissue without any addition and measured the fluorescence reduction after the addition of SDX-DS, SDS-HEP and parnaparin.

TABLE 13

| | Concentration (μg/ml) | Reduction of Intensity % |
|---|---|---|
| Sulodexide | 24 | 50 |
| SDX-DS | 5 | 80 |
| Parnaparin | 19 | 50 |

The invention claimed is:

1. A method to treat a patient, the method comprising:
   administering to the patient a sulodexide extracted component dermatan sulfate and/or low molecular weight heparin, or a mixture thereof, or a pharmaceutically acceptable salt, solvate, hydrate, clathrate thereof to treat a pathology involving matrix metalloproteinases (MMPs).

2. The method according to claim 1, wherein said component is a dermatan sulfate.

3. The method according to claim 1, wherein said component is a low molecular weight heparin.

4. The method according to claim 1 wherein the MMPs is MMP-9.

5. The method according to claim 1, wherein said pathology is an infection or a neoplastic disease.

6. The method according to claim 1, wherein said pathology is selected from the group consisting of vascular disease, gastrointestinal ulcers, cardiovascular disease caused by diabetes, pathogenesis of inflammation, venous relaxing, increase and progression of the tumor, growing in the primary tumor, angiogenesis, extravasation and intravasation of the neoplastic cells and combination thereof.

7. The method according to claim 6, wherein said vascular disease is selected from the group consisting of chronic venous insufficiency (CVI), varicose veins, cardiac break after myocardium infarct, abdominal aortic aneurysm.

8. The method according to claim 1 wherein an inhibition or a reduction of MMPs is in a quantity of higher than 20%.

9. The method according to claim 8 wherein the MMP inhibited or reduced is MMP-9 and the inhibition or reduction is in a quantity of higher than 20%.

10. The method of claim 1 wherein the sulodexide extracted component, or mixture thereof, further comprises sulodexide.

11. The method according to claim 2, wherein said sulodexide extracted component dermatan sulfate is administered in a dosage of at least 1 mg/day.

12. The method according to claim 2, wherein said sulodexide extracted component dermatan sulfate is administered in a dosage between 4 mg/day and 300 mg/day.

13. The method according to claim 2, wherein said sulodexide extracted component dermatan sulfate is administered in a dosage greater than 300 mg/day.

14. The method according to claim 3, wherein said sulodexide extracted component low molecular weight heparin is administered in a dosage of at least 16 mg/day together with sulodexide extracted component dermatan sulfate.

15. The method according to claim 3, wherein said sulodexide extracted component low molecular weight heparin is administered in a dosage between 19 mg/day and 800 mg/day together with sulodexide extracted component dermatan sulfate.

16. The method according to claim 3, wherein said sulodexide extracted component low molecular weight heparin is administered in a dosage greater than 900 mg/day together with sulodexide extracted component dermatan sulfate.

17. The method according to claim 1, wherein said mixture is a composition wherein said sulodexide extracted component dermatan sulfate is comprised at a concentration of about 20% by weight and said sulodexide extracted component low molecular weight heparin is comprised at a concentration of about 80% by weight.

* * * * *